(12) United States Patent
Lipford et al.

(10) Patent No.: US 8,546,550 B2
(45) Date of Patent: Oct. 1, 2013

(54) IMMUNOSTIMULATORY OLIGONUCLEOTIDES

(75) Inventors: Grayson B. Lipford, Watertown, MA (US); Christopher Fraser, Arlington, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days.

(21) Appl. No.: 13/298,173

(22) Filed: Nov. 16, 2011

(65) Prior Publication Data

US 2012/0213812 A1 Aug. 23, 2012

Related U.S. Application Data

(60) Provisional application No. 61/414,194, filed on Nov. 16, 2010.

(51) Int. Cl.
*C07H 21/02* (2006.01)

(52) U.S. Cl.
USPC ........................................ 536/23.1; 514/44 R

(58) Field of Classification Search
None
See application file for complete search history.

(56) References Cited

U.S. PATENT DOCUMENTS

| | | |
|---|---|---|
| 2002/0028784 A1 | 3/2002 | Nest |
| 2003/0148976 A1 | 8/2003 | Krieg et al. |
| 2010/0184834 A1 | 7/2010 | Dina et al. |

OTHER PUBLICATIONS

International Search Report issued in PCT/US2011/61056 mailed Mar. 22, 2012.
Written Opinion of the International Searching Authority in PCT/US2011/61056 mailed Mar. 22, 2012.
Marshall et al., "Superior activity of the type C class of ISS in vitro and in vivo across multiple species," DNA and Cell Biology, 24(2):23-79 (2005).
Higgins et al., "Immunostimulatory DNA as a vaccine adjuvant," Expert Rev. Vaccines, 6:747-759 (2007).

*Primary Examiner* — Jennifer Pitrak McDonald
(74) *Attorney, Agent, or Firm* — Fish & Richardson P.C.

(57) ABSTRACT

Compositions that include immunostimulatory nucleic acids are disclosed, along with the use of such compositions to induce immune responses.

27 Claims, 5 Drawing Sheets

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tcgtcgaacg ttcgcgaacg ttcg                                    24

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
tcgtcgaacg ttcgcgaacg ttcgaacgtt                              30

```
<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
tcgtcgaacg ttcgcgaacg ttcgaacgtt aacgtt                              36

<210> SEQ ID NO 4
<211> LENGTH: 48
<212> TYPE: DNA
<213> ORGANISM: Artificial Sequence
<220> FEATURE:
<223> OTHER INFORMATION: Synthetic

<400> SEQUENCE: 4
tcgtcgaacg ttcgcgaacg ttcgtcgtcg aacgttcgcg aacgttcg                 48

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
tcgtcgaacg ttcgcgaacg ttcgttcgaa                                     30

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
tcgtcgaacg ttcgcgaacg ttcggacgtc                                     30

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
tcgtcgaacg ttcgcgaacg ttcgatcgat                                     30

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tcgtcgtttt cggcgcgcgc cg                                             22
```

US 8,546,550 B2

IMMUNOSTIMULATORY OLIGONUCLEOTIDES

CROSS-REFERENCE TO RELATED APPLICATIONS

This application claims priority to U.S. Application Ser. No. 61/414,194, filed on Nov. 16, 2010. The contents of the prior application are incorporated by reference herein in their entirety.

BACKGROUND

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen-associated molecular patterns (PAMPs). Compositions and methods useful for modulating innate immunity are therefore of great interest, as they can affect therapeutic approaches to conditions involving autoimmunity, inflammation, allergy, asthma, graft rejection, graft versus host disease (GvHD), infection, cancer, and immunodeficiency, etc.

Recently there have been a number of reports describing the immunostimulatory effect of certain types of nucleic acid molecules, including CpG nucleic acids, GU rich ssRNA and double-stranded RNA. Of note, it has been reported that Toll-like receptor 9 (TLR9) recognizes bacterial DNA and oligonucleotides containing a CpG motif wherein the cytosine is unmethylated. See, e.g., Hemmi H et al. (2000) Nature 408: 740-5; Bauer S. et al. (2001) Proc Natl Acad Sci USA 98:9237-42. The effects of CpG containing oligonucleotides on immune modulation have been described in U.S. patents such as U.S. Pat. Nos. 6,194,388; 6,207,646; 6,239,116; and 6,218,371; and published international patent applications, such as WO 98/37919, WO 98/40100, WO 98/52581, and WO 99/56755.

However, additional specific nucleic acid sequences capable of immunostimulatory action are desirable to provide immune stimulation in a variety of contexts. Therefore, what is needed are compositions and related methods that encompass such novel immunostimulatory nucleic acids.

SUMMARY

The inventors have that the problems and limitations noted above can be overcome by practicing the inventions disclosed herein. In particular, the inventors have discovered that it is possible to provide compositions, and related methods, that include an immunostimulatory isolated nucleic acid molecule comprising a sequence:

```
                                          [SEQ ID NO: 1]
    5'-TCGTCGAACGTTCGCGAACGTTCG-3';
``` wherein at least one C is unmethylated, and optionally a pharmaceutically acceptable excipient.

The immunostimulatory nucleic acids can include one or more stabilizing modifications, e.g., modifications of 3' OH or 5' OH groups, modifications of nucleotide bases, modifications of sugar components, and/or modifications of phosphate groups. The stabilizing modification can include the use of a phosphorothioate backbone. In some implementations, the immunostimulatory nucleic acids do not include a stabilizing modification.

The compositions can further include an antigen, e.g., a B cell antigen or a T cell antigen. A T cell antigen can include a T helper cell antigen. Exemplary B cell antigens include one or more of a protein, peptide, small molecule, and a carbohydrate.

The compositions can further include a carrier (e.g., a protein carrier or a synthetic nanocarrier) coupled (e.g., covalently or non-covalently) to the immunostimulatory nucleic acid. The synthetic nanocarrier can additionally be coupled (e.g., covalently or non-covalently) to an antigen. The compositions can further include an additional synthetic nanocarrier that is not coupled to the immunostimulatory isolated nucleic acid. The additional synthetic nanocarrier can, e.g., be coupled to an antigen (e.g., a T helper cell antigen).

The disclosure also provides nucleic acids that include the sequence of SEQ ID NO:1.

The disclosure further provides methods that include administering a composition or nucleic acid disclosed herein to a subject.

The disclosure further provides methods of inducing IL-6 production in a subject, that include administering to the subject a composition or nucleic acid disclosed herein in an amount effective amount to induce IL-6 in the subject.

The disclosure further provides methods of inducing interferon-alpha in a subject, that include administering to the subject a composition or nucleic acid disclosed herein in an amount effective amount to induce interferon-alpha in the subject.

The disclosure further provides methods of inducing IP-10 in a subject, that include administering to the subject a composition or nucleic acid disclosed herein in an amount effective amount to induce IP-10 in the subject.

The disclosure further provides vaccines that include the compositions and nucleic acids disclosed herein.

The disclosure further provides methods that include administering to a subject a composition disclosed herein that includes an antigen in an amount effective to induce an antibody response against the antigen in the subject. The disclosure further provides the use of a composition disclosed herein that includes an antigen to induce an antibody response against the antigen in a subject. The disclosure further provides compositions as disclosed herein that include an antigen for use in inducing an antibody response against the antigen in a subject.

The disclosure further provides immunostimulatory compositions and compositions for inducing an antibody response against an antigen in a subject that include the compositions and nucleic acids disclosed herein.

Before describing the present inventions in detail, it is to be understood that this invention is not limited to particularly exemplified materials or process parameters as such can, of course, vary. It is also to be understood that the terminology used herein is for the purpose of describing particular implementations of the inventions only, and is not intended to be limiting of the use of alternative terminology to describe the present inventions.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a solvent" includes a mixture of two or more such solvents, reference to "an adhesive" includes mixtures of two or more such materials, and the like.

The details of one or more implementations of the invention are set forth in the accompanying drawings and the description below. Other features, objects, and advantages of the invention will be apparent from the description and drawings, and from the claims.

DETAILED DESCRIPTION

Figure 1A:
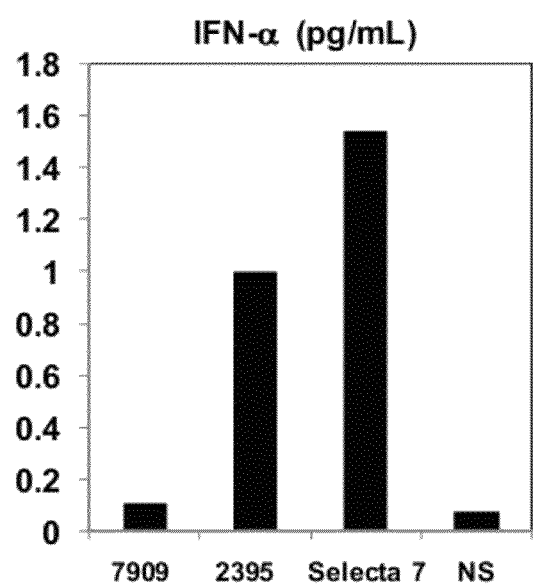
FIGS. 1A-1B are bar graphs depicting cytokine levels (1A, IFN-α; 1B, IL-6) as measured by ELISA of peripheral blood mononuclear cells stimulated in the presence of the indicated CpG oligonucleotides or the absence (NS) of oligonucleotide.

This disclosure provides compositions, and related methods, that include an immunostimulatory isolated nucleic acid molecule comprising a sequence:

[SEQ ID NO: 1]
5'-TCGTCGAACGTTCGCGAACGTTCG-3';

wherein at least one C is unmethylated, and optionally a pharmaceutically acceptable excipient.

Distinct functional classes of immunostimulatory CpG nucleic acids have been identified. Class A (A-type) CpG nucleic acids activate natural killer (NK) cells and stimulate the maturation of dendritic cells and induce production of IP-10 and type I interferons (including IFNα). Class B (B-type) CpG nucleic acids are strong stimulators of human B cell and monocyte maturation, stimulating the production of IL-6 (but not type I interferons).

These functional differences are reflected in distinct structural features: Class A polynucleotides exhibit a poly G sequence at either or both of the 5' and 3' ends with an internal palindrome sequence containing GC dinucleotides, while Class B polynucleotides contain one or more of the hexameric motif: 5'-Pu Py C G Py Pu-3'.

More recently, Class C(C-type) CpG nucleic acids have been described which combine the properties of both Class A and Class B. Class C polynucleotides therefore activate NK cells and stimulate the production of IL-6, IFNα and IP-10 as well as the maturation of dendritic cells, B cells and monocytes.

This broad immunostimulation of both innate and adaptive components of the immune system is of profound clinical importance and there is currently a need for further C-type immunostimulatory polynucleotides.

To this end, certain rules have been formulated (and particular structural motifs identified) for C-type polynucleotides. For example, WO 03/015711 identifies a combination of a stimulatory motif (such as a CpG motif or the sequence TCGTCG) with either a CG-rich (at least two-thirds G and C) palindrome or a neutralizing motif, and describes the 22-mer oligodeoxynucleotide (ODN) 2395 (now regarded as a prototypical type-C ODN). ODN 2395 has the following phosphorothioate-linked sequence:

[SEQ ID NO: 8]
5'-tcgtcgttttcggcgcgcgccg-3'.

Later attempts to expand the range of C-type oligonucleotides applied different rules and structural templates. For example, WO 05/042018 describes structurally distinct C-class CpG oligonucleotides with an imperfect palindrome at or near the 3' end which are designed to form duplex or higher-order structures in vivo.

However, the structure-function relationships governing the activity of C-type oligonucleotides remain unclear and there remains a need for empirical testing of large numbers of sequence variants.

The present inventors have unexpectedly discovered that nucleic acids that do not conform to the above rules and which comprise the sequence:

[SEQ ID NO: 1]
5'-TCGTCGAACGTTCGCGAACGTTCG-3';

exhibit potent C-type immunostimulatory activity.

The Examples illustrate the biological activity of an implementation of the present inventions, and also several different nucleic acid sequences and compositions useful in the present inventions described herein. Example 1, in particular, provides support for the classification of nucleic acids that comprise SEQ ID NO:1 as C-type immunostimulatory nucleic acids.

According to a first aspect of the present invention there are provided C-type immunostimulatory nucleic acids comprising the sequence:

[SEQ ID NO: 1]
5'-TCGTCGAACGTTCGCGAACGTTCG-3';

wherein at least one C (e.g., one, two, three, four, five, six or all seven C's) is unmethylated.

The nucleic acids can be isolated.

Alternatively, or in addition, the nucleic acids can meet the terms of the length parameters set out herein.

Thus, the nucleic acids can have a length in the range of between 24 and 100 nucleotides. In some implementations the length is in the range of 24-30, 24-40, 24-50, 24-60, 24-70, 24-80 or 24-90 nucleotides.

The nucleic acids as defined above can consist, or consist essentially, of the sequence:

[SEQ ID NO: 1]
5'-TCGTCGAACGTTCGCGAACGTTCG-3'.

The nucleic acids as defined in any one of the preceding paragraphs can further comprise a 5' sequence extension. In such implementations, the nucleic acids can retain a TCGTCG hexamer as the 5' terminus.

The nucleic acids as defined in any one of the preceding paragraphs can further comprise a 3' sequence extension.

Thus, the nucleic acids as defined in any one of the preceding paragraphs can further comprise both 5' and 3' sequence extensions.

According to a second aspect of the present inventions, there are provided compositions comprising the nucleic acids of the first aspect of the inventions as defined in any one of the preceding paragraphs.

The compositions of the second aspect can be pharmaceutical compositions which further comprise one or more pharmaceutically acceptable excipients.

The compositions of the second aspect can further comprise one or more antigens, e.g., as defined herein.

The compositions of the second aspect can further comprise one or more carriers (e.g., as defined herein) coupled to the immunostimulatory nucleic acid.

According to a third aspect of the present inventions there are provided vaccines comprising the nucleic acids described herein. The vaccines can further comprise one or more antigens.

According to a fourth aspect of the present inventions there are provided nucleic acids as defined herein and in any of the preceding paragraphs for use in therapy or prophylaxis.

In the fourth aspect of the inventions, the nucleic acids as defined herein and in any of the preceding paragraphs are used in: (a) vaccination (for example prophylactic or therapeutic vaccination); (b) the induction of IL-6 production in a subject; (c) the induction of type I interferon (e.g., IFNα) production in a subject; (d) the induction of type II interferon (e.g., IFNγ) in a subject; (e) the induction of IP-10 production in a subject; (f) activating endogenous NK cells in a subject; (g) stimulating endogenous dendritic cells in a subject; (h) stimulating endogenous B cells in a subject; (i) stimulating endogenous monocytes in a subject; (j) the treatment or prophylaxis of an infection, for example a bacterial, viral, fungal, or metazoan infection; (k) the treatment or prophylaxis of an allergic condition (e.g., asthma); (l) the treatment or prophylaxis of cancer; (m) inducing, enhancing, modulating, directing, or redirecting an immune response; (n) the treatment or prophylaxis of metabolic diseases; (o) the treatment or prophylaxis of degenerative diseases; (p) the treatment or prophylaxis of autoimmune diseases; (q) the treatment or prophylaxis of inflammatory diseases; (r) the treatment or prophylaxis of immunological diseases, disorders and/or conditions; (s) the treatment or prophylaxis of an addiction (for example an addiction to nicotine or a narcotic); or (t) the treatment or prophylaxis of a condition resulting from the exposure to a toxin, hazardous substance, environmental toxin, or other harmful agent.

Further prophylactic and therapeutic uses of the nucleic acids described herein are described in more detail below.

In each of the above aspects as defined in the preceding paragraphs, the nucleic acids can comprise modifications, e.g., stabilizing modifications. Such stabilizing modifications can comprise modifications of 3' OH or 5' OH groups, modifications of nucleotide bases, modifications of sugar components, or modifications of phosphate groups. In some implementations, the stabilizing modification comprises a phosphorothioate backbone.

Yet other aspects of the inventions are as defined in the claims appended hereto.

The inventions will now be described in more detail below.

Definitions

"Adjuvant" means an agent that does not constitute a specific antigen, but boosts the strength and longevity of immune response to a co-administered antigen. Such adjuvants can include, but are not limited to, stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherichia coli, Salmonella minnesota, Salmonella typhimurium*, or *Shigella flexneri* or specifically with MPL® (AS04), MPL A of above-mentioned bacteria separately, saponins, such as QS-21,Quil-A, ISCOMs, ISCOMA-TRIX™, emulsions such as MF59™, Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of *N. gonorrheae, Chlamydia trachomatis*, and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments.

In implementations, adjuvants comprise agonists for pattern recognition receptors (PRR), including, but not limited to Toll-Like Receptors (TLRs), specifically TLRs 2, 3, 4, 5, 7, 8, 9 and/or combinations thereof. In other implementations, adjuvants comprise agonists for Toll-Like Receptors 3, agonists for Toll-Like Receptors 7 and 8, or agonists for Toll-Like Receptor 9; preferably the recited adjuvants comprise imidazoquinolines; such as R848; adenine derivatives, such as those disclosed in U.S. Pat. No. 6,329,381 (Sumitomo Pharmaceutical Company); immunostimulatory DNA; or immunostimulatory RNA. In specific implementations, the inventive compositions incorporate as adjuvants compounds that are agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to, imidazoquinoline amines, imidazopyridine amines, 6,7-fused cycloalkylimidazopyridine amines, and 1,2-bridged imidazoquinoline amines.

Useful adjuvants include imiquimod and resiquimod (also known as R848). In specific implementations, an adjuvant can be an agonist for the surface molecule CD40. In certain implementations, to stimulate immunity rather than tolerance, an inventive composition incorporates an adjuvant that promotes DC maturation (needed for priming of naive T cells) and the production of cytokines, such as type I interferons, which promote antibody immune responses. In implementations, adjuvants can also include immunostimulatory RNA molecules, such as, but not limited to, dsRNA or poly I:C (a TLR3 stimulant), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006/0241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some implementations, an adjuvant can be a TLR-4 agonist, such as bacterial lipopolysaccharide (LPS), VSV-G, and/or HMGB-1. In some implementations, adjuvants can comprise TLR-5 agonists, such as flagellin, or portions or derivatives thereof, including but not limited to those disclosed in U.S. Pat. Nos. 6,130,082, 6,585,980, and 7,192,725.

In specific implementations, the inventive compositions incorporate a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374: 546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al. "Immunostimulatory DNA sequences function as T helper-1-promoting adjuvants," Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., "Bacterial DNA as immune cell activator," Trends Microbiol. 1998. 6:496-500; U.S. Pat. No. 6,207,646 to Krieg et al.; U.S. Pat. No. 7,223,398 to Tuck et al.; U.S. Pat. No. 7,250,403 to Van Nest et al.; or U.S. Pat. No. 7,566,703 to Krieg et al. In preferred implementations wherein an adjuvant comprises a ligand for Toll-like receptor (TLR)-9, such as immunostimulatory DNA molecules comprising CpGs, the immunostimulatory DNA molecules do not comprise nucleic acids that comprise SEQ ID NO:1.

In some implementations, adjuvants can be proinflammatory stimuli released from necrotic cells (e.g., urate crystals). In some implementations, adjuvants can be activated components of the complement cascade (e.g., CD21, CD35, etc.). In some implementations, adjuvants can be activated components of immune complexes. The adjuvants can also include complement receptor agonists, such as a molecule that binds to CD21 or CD35. In some implementations, the complement receptor agonist induces endogenous complement opsonization of the synthetic nanocarrier. In some implementations, adjuvants are cytokines, which are small proteins or biological factors (in the range of 5 kD-20 kD) that are released by cells and have specific effects on cell-cell interaction, communication and behavior of other cells. In some implementations, the cytokine receptor agonist is a small molecule, antibody, fusion protein, or aptamer.

In various implementations, at least a portion of the dose of adjuvant can be coupled to synthetic nanocarriers, e.g., all of the dose of adjuvant can be coupled to synthetic nanocarriers. In other implementations, at least a portion of the dose of the adjuvant is not coupled to the synthetic nanocarriers. In certain implementations, the dose of adjuvant comprises two or more types of adjuvants. For instance, and without limitation, adjuvants that act on different TLR receptors can be combined. As an example, in an implementation a TLR 7/8 agonist can be combined with a TLR 9 agonist. In another implementation, a TLR 7/8 agonist can be combined with a TLR 9 agonist. In yet another implementation, a TLR 9 agonist can be combined with a TLR 9 agonist.

"Administering" or "administration" means providing a drug to a subject in a manner that is pharmacologically useful.

"Antigen" means a B cell antigen or T cell antigen. In certain implementations, antigens are coupled to the synthetic nanocarriers. In other implementations, antigens are not coupled to the synthetic nanocarriers. In implementations antigens are coadministered with the synthetic nanocarriers. In other implementations antigens are not coadministered with the synthetic nanocarriers. "Type(s) of antigens" means molecules that share the same, or substantially the same, antigenic characteristics.

"B cell antigen" means any antigen that is or recognized by and triggers an immune response in a B cell (e.g., an antigen that is specifically recognized by a B cell receptor on a B cell). In some implementations, an antigen that is a T cell antigen is also a B cell antigen. In other implementations, the T cell antigen is not also a B cell antigen. B cell antigens include, but are not limited to proteins, peptides, small molecules (meaning molecules with a weight average molecular weight of less than 10,000), and carbohydrates. In some implementations, the B cell antigen is a non-protein antigen (i.e., not a protein or peptide antigen). In some implementations, the B cell antigen is a carbohydrate associated with an infectious agent. In some implementations, the B cell antigen is a glycoprotein or glycopeptide associated with an infectious agent. The infectious agent can be a bacterium, virus, fungus, protozoan, or parasite. In some implementations, the B cell antigen is a poorly immunogenic antigen. In some implementations, the B cell antigen is an abused substance or a portion thereof. In some implementations, the B cell antigen is an addictive substance or a portion thereof. Addictive substances include, but are not limited to, nicotine, a narcotic, a cough suppressant, a tranquilizer, and a sedative. In some implementations, the B cell antigen is a toxin, such as a toxin from a chemical weapon or natural sources. The B cell antigen can also be a hazardous environmental agent. In some implementations, the B cell antigen is a self antigen. In other implementations, the B cell antigen comprises an alloantigen, an allergen, a contact sensitizer, a degenerative disease antigen, a hapten, an infectious disease antigen, a cancer antigen, an atopic disease antigen, an autoimmune disease antigen, an addictive substance, a xenoantigen, or a metabolic disease enzyme or enzymatic product thereof.

"Carrier" means a substance that can be co-administered with the inventive immunostimulatory isolated nucleic acid, and that can alter in vivo characteristics of the inventive immunostimulatory isolated nucleic acid, such as pharmacokinetics, stability and trafficking Carriers differ from pharmaceutically acceptable excipients in that pharmaceutically acceptable excipients comprise pharmacologically inactive materials, while carriers comprise materials that can alter the in vivo characteristics of the inventive immunostimulatory isolated nucleic acid. In various implementations, carriers can comprise nanocarriers comprising PLG, PLGA, or silica; perfluorocarbon(s); lipids; gelatin; chitosan; or cyclodextrin. In other implementations, carriers can also comprise proteins such as albumin, collagen, or diphtheria CRM197 protein.

"Coadministered" means administering two or substances to a subject in a manner that is correlated in time. In implementations, coadministration can occur through administration of two or more substances in the same dosage form. In other implementations, coadministration can encompass administration of two or more substances in different dosage forms, but within a specified period of time, e.g., within 1 month, within 1 week, within 1 day, or within 1 hour.

"Couple" or "Coupled" or "Couples" (and the like) means to chemically associate one entity (for example a moiety) with another. In some implementations, the coupling is covalent, meaning that the coupling occurs in the context of the presence of a covalent bond between the two entities. In non-covalent implementations, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In implementations, encapsulation is a form of coupling.

"C-type immunostimulatory nucleic acid" is a nucleic acid containing at least one unmethylated CpG, and which can stimulate the production of inter alia IL-6, IP-10, and IFNα in vivo, and can stimulate plasmacytoid dendritic cells.

"Encapsulate" means to enclose within a synthetic nanocarrier, preferably enclose completely within a synthetic nanocarrier. Most or all of a substance that is encapsulated is not exposed to the local environment external to the synthetic nanocarrier. Encapsulation is distinct from absorption, which places most or all of a substance on a surface of a synthetic nanocarrier, and leaves the substance exposed to the local environment external to the synthetic nanocarrier.

"Immunostimulatory" means that a substance has a stimulatory effect on the immune system. Such substances can be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) Nature 374:546-549; Yamamoto et al. (1992) J. Immunol. 148:4072-76; Ballas et al. (1996) J. Immunol. 157:1840-45; Klinman et al. (1997) J. Immunol. 158:3635-39; Sato et al. (1996) Science 273:352-354; Pisetsky (1996) J. Immunol. 156:421-423; Shimada et al. (1986) Jpn. J. Cancer Res. 77:808-816; Cowdery et al. (1996) J. Immunol. 156:4570-75; Roman et al. (1997) Nat. Med. 3:849-854; Lipford et al. (1997a) Eur. J. Immunol. 27:2340-44; WO 98/55495 and WO 00/61151. Accordingly, these and other methods can be used to identify, test and/or confirm immunostimulatory substances, such as immunostimulatory nucleotides, preferably immunostimulatory isolated nucleic acids.

"Isolated nucleic acid" means a nucleic acid that is synthesized or separated from its native environment and present in sufficient quantity to permit its identification or use. An isolated nucleic acid can be one that is (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. Isolated nucleic acids can be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

An isolated nucleic acid can be substantially purified, but need not be. For example, a nucleic acid that is isolated within a cloning or expression vector is not pure in that it can comprise only a tiny percentage of the material in the cell in which it resides. Such a nucleic acid is isolated, however, as the term is used herein because it is readily manipulable by standard techniques known to those of ordinary skill in the art. Any of the nucleic acids provided herein can be isolated. In the context of the present invention, nucleic acid is used interchangeably with the term polynucleic acid, which is intended to encompass compounds comprising multiple nucleic acid residues.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an implementation, a minimum dimension of at least 75%, preferably 80%, more preferably 90%, of the synthetic nanocarriers in a sample, based on the total number of synthetic nanocarriers in the sample, is greater than 100 nm. In an implementation, a maximum dimension of at least 75%, preferably 80%, more preferably 90%, of the synthetic nanocarriers in a sample, based on the total number of synthetic nanocarriers in the sample, is equal to or less than 5 μm. Preferably, a minimum dimension of at least 75%, preferably 80%, more preferably 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers can vary depending on the implementation. For instance, aspect ratios of the maximum to minimum dimensions of the synthetic nanocarriers can vary from 1:1 to 1,000, 000:1, preferably from 1:1 to 100, 000:1, more preferably from 1:1 to 1000:1, still preferably from 1:1 to 100:1, and yet more preferably from 1:1 to 10:1. Preferably, a maximum dimension of at least 75%, preferably 80%, more preferably 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred implementations, a maximum dimension of at least 75%, preferably 80%, more preferably 90%, of the synthetic nanocarriers in a sample, based on the total number of synthetic nanocarriers in the sample, is equal to or greater than 100 nm, more preferably equal to or greater than 120, more preferably greater than 130 nm, more preferably greater than 140 nm, and more preferably still greater than 150 nm. Measurement of synthetic nanocarrier sizes is obtained by suspending the synthetic nanocarriers in a liquid (usually aqueous) media and using dynamic light scattering (e.g., using a Brookhaven ZetaPALS instrument).

"Nucleic acid" in the context of the immunostimulatory nucleic acids of the invention means a string of linked nucleotides or modified nucleotides. The sugar moieties can be ribose, deoxyribose or any of the various modified sugars as described herein (including combinations thereof). The base moieties can be any purine or pyrimidine bases, including C, A, T, G, U and any of the modified bases as described herein (including combinations thereof). The nucleic acids can be linked by natural phosphodiester bonds, or by any of the other linkages described herein (including for example phosphorothioate links, so exhibiting a modified backbone), including combinations thereof. The nucleic acid can be single or double stranded, and can be of any topology/conformation (including branched, circular and hairpin). Modification of the nucleic acids of the invention with such modified sugars, bases and/or backbones are preferably stabilizing modifications, as described herein.

"Pharmaceutically acceptable excipient" means a pharmacologically inactive material used to formulate the inventive compositions. Pharmaceutically acceptable excipients comprise a variety of materials known in the art, including, but not limited to, reconstitution aids, colorants, saline, inorganic or organic buffers (e.g., sodium or potassium salts of phosphate, carbonate, acetate, or citrate; including phosphate buffered saline), pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

"Subject" means humans and animals, including warm blooded mammals such as primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain implementations the synthetic nanocarriers do not comprise albumin nanoparticles. In implementations, inventive synthetic nanocarriers do not comprise chitosan.

A synthetic nanocarrier can be, but is not limited to, one or a plurality of lipid-based nanoparticles, polymeric nanoparticles, metallic nanoparticles, surfactant-based emulsions, dendrimers, buckyballs, nanowires, virus-like particles, peptide or protein-based particles (such as albumin nanoparticles) and/or nanoparticles that are developed using a combination of nanomaterials such as lipid-polymer nanoparticles. Synthetic nanocarriers can be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 2006/0002852 to Saltzman et al., (3) the lithographically constructed nanoparticles of Published US Patent Application 2009/0028910 to DeSimone et al., (4) the disclosure of WO 2009/051837 to von Andrian et al., or (5) the nanoparticles disclosed in Published US Patent Application 2008/0145441 to Penades et al. In implementations, synthetic nanocarriers can possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than 100 nm, preferably equal to or less than about 100 nm, do not comprise a surface with hydroxyl groups that activate complement or alternatively comprise a surface that consists essentially of moieties that are not hydroxyl groups that activate complement. In certain implementations, synthetic nanocarriers as described herein that have a minimum dimension of equal to or less than about 100 nm, e.g., equal to or less than about 100 nm, do not comprise a surface that substantially activates complement or alternatively comprise a surface that consists essentially of moieties that do not substantially activate complement. In a more preferred implementation, synthetic nanocarriers according to the invention that have a minimum dimension of equal to or less than about 100 nm, preferably equal to or less than about 100 nm, do not comprise a surface that activates complement or alternatively comprise a surface that consists essentially of moieties that do not activate complement. In implementations, synthetic nanocarriers exclude virus-like particles (VLPs). In implementations, when synthetic nanocarriers comprise virus-like particles, the virus-like particles comprise non-natural adjuvant (meaning that the VLPs comprise an adjuvant other than naturally occurring RNA generated during the production of the VLPs). In implementations, synthetic nanocarriers can possess an aspect ratio greater than 1:1, 1:1.2, 1:1.5, 1:2, 1:3, 1:5, 1:7, or greater than 1:10.

"T cell antigen" means any antigen that is recognized by and triggers an immune response in a T cell (e.g., an antigen that is specifically recognized by a T cell receptor on a T cell or an NKT cell via presentation of the antigen or portion thereof bound to a Class I or Class II major histocompatability complex molecule (MHC), or bound to a CD1 complex. In some implementations, an antigen that is a T cell antigen is also a B cell antigen. In other implementations, the T cell antigen is not also a B cell antigen. T cell antigens generally are proteins or peptides. T cell antigens can be an antigen that stimulates a CD8+ T cell response, a CD4+ T cell response, or both. The nanocarriers, therefore, in some implementations can effectively stimulate both types of responses. In implementations, T cell antigens can comprise one or more of the following: Tetanus:TT830-843, TT947-967; Diphtheria DT331-350, Adenovirus H910-924; CMV pp 65, Measles F288-302, F421-435, F256-270, NP335-345; HCV A1248-1261, C1781-1800,D2571-2590; Influenza HA91-108, HA307-319, HA354-372.

In some implementations the T cell antigen is a T helper cell antigen (i.e., one that can generate an enhanced response to an unrelated B cell antigen through stimulation of T cell help). In implementations, a T helper cell antigen can comprise one or more peptides obtained or derived from tetanus toxoid, Epstein-Barr virus, influenza virus, respiratory syncytial virus, measles virus, mumps virus, rubella virus, cytomegalovirus, adenovirus, diphtheria toxoid, or a PADRE peptide (known from the work of Sette et al. U.S. Pat. No. 7,202,351). In other implementations, a T helper cell antigen can comprise one or more lipids, or glycolipids, including but not limited to: α-galactosylceramide (α-GalCer), α-linked glycosphingolipids (from *Sphingomonas* spp.), galactosyl diacylglycerols (from *Borrelia burgdorferi*), lypophosphoglycan (from *Leishmania* donovani), and phosphatidylinositol tetramannoside (PIM4) (from *Mycobacterium leprae*).

For additional lipids and/or glycolipids useful as a T helper cell antigen, see V. Cerundolo et al., "Harnessing invariant NKT cells in vaccination strategies." Nature Rev Immun, 9:28-38 (2009). In implementations, CD4+ T-cell antigens can be derivatives of a CD4+ T-cell antigen that is obtained from a source, such as a natural source. In such implementations, CD4+ T-cell antigen sequences, such as those peptides that bind to MHC II, can have at least 70%, 80%, 90%, or 95% identity to the antigen obtained from the source. In implementations, the T cell antigen, preferably a T helper cell antigen, can be coupled to, or uncoupled from, a synthetic nanocarrier.

"Vaccine" means a composition of matter that improves the immune response to a particular pathogen or disease. A vaccine typically contains factors that stimulate a subject's immune system to recognize a specific antigen as foreign and eliminate it from the subject's body. A vaccine also establishes an immunologic 'memory' so the antigen will be quickly recognized and responded to if a person is re-challenged. Vaccines can be prophylactic (for example to prevent future infection by any pathogen), or therapeutic (for example a vaccine against a tumor specific antigen for the treatment of cancer). In implementations, a vaccine can comprise dosage forms according to the invention.

Nucleic Acids

In implementations, the invention encompasses compositions comprising an immunostimulatory isolated nucleic acid comprising:

[SEQ ID NO: 1]
5'-TCGTCGAACGTTCGCGAACGTTCG-3'.

In implementations, the inventive compositions comprise from 0.001 micrograms to 100,000 micrograms of the recited oligonucleotide; 0.01 micrograms to 10,000 micrograms of the recited oligonucleotide; 0.1 micrograms to 1,000 micrograms of the recited oligonucleotide; 1 microgram to 500 micrograms of the recited oligonucleotides, or 1 microgram to 200 micrograms of the recited oligonucleotides. In certain implementations, none of the recited oligonucleotides are absorbed on a surface of the synthetic nanocarriers.

In implementations, the immunostimulatory isolated nucleic acids of the present inventions generate a cytokine response pattern characteristic of a "C-type" CpG-containing nucleic acids. This cytokine pattern can be distinguished from a "B-type" CpG containing nucleic acid because both B- and C-types induce expression of IL-6, while only C-types also induce expression of interferon-alpha and IP-10. Accordingly, and as seen in the Examples, in various implementations, the recited nucleic acids induce IL-6 production in a subject when any of the inventive compositions are administered to the subject in an amount effective to induce IL-6 in the subject. In certain implementations, the recited nucleic acids induce interferon-alpha in a subject when any of the inventive compositions are administered to the subject in an amount effective to induce interferon-alpha production in the subject. In some implementations, the recited nucleic acids induce IP-10 in a subject when any of the inventive compositions are administered to the subject in an amount effective to induce IP-10 production in the subject.

In certain implementations, the recited nucleic acids do not comprise stabilizing modifications, preferably such nucleic acids comprise a phosphodiester backbone.

In implementations, the recited nucleic acids can contain stabilizing modifications. Stabilizing modifications of the nucleic acids include any known in the art, but are not limited to, modifications of the 3' OH or 5' OH group, modifications of the nucleotide base, modifications of the sugar component, and modifications of the phosphate group. Various such stabilizing modifications are described herein, and can also be found in Published US Patent Application 2008/0207550 to Fearon et al., or U.S. Pat. No. 6,239,116 to Krieg et al.

The recited nucleic acids can be single stranded or double stranded DNA, and/or can comprise additional flanking sequences. The recited nucleic acids can contain naturally-occurring or modified, non-naturally occurring bases, and can contain modified sugar, phosphate, and/or termini. For example, phosphate modifications include, but are not limited to, methyl phosphonate, phosphorothioate, alkylphosphonothioate, e.g., —O—P=O(—S—$CH_2CO_2$—), phosphoramidate (bridging or non-bridging), phosphotriester and phosphorodithioate, and alkylphosphorodithioate as above and can be used in any combination. Other non-phosphate linkages can also be used. In a useful implementation, modified nucleic acids of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, can also be made and combined with any phosphate modification. Examples of base modifications (discussed further below) include, but are not limited to, addition of an electron-withdrawing moiety to C-5 and/or C-6 of a cytosine of the nucleic acid (e.g., 5-bromocytosine, 5-chlorocytosine, 5-fluorocytosine, 5-iodocytosine) and C-5 and/or C-6 of a uracil of the nucleic acid (e.g., 5-bromouracil, 5-chlorouracil, 5-fluorouracil, 5-iodouracil). See, for example, International Patent Application No. WO 99/62923.

Synthesis of nucleic acids containing modified phosphate linkages or non-phosphate linkages is known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group), which can be attached to the sugar or sugar analog moiety in the nucleic acid of the present inventions, can be a monophosphate, diphosphate, triphosphate, alkylphosphonate, phosphorothioate, phosphorodithioate, phosphoramidate, or the like. The preparation of the above-noted phosphate analogs, and their incorporation into nucleic acids, per se, is also known and need not be described here in detail. Peyrottes et al. (1996) Nucleic Acids Res. 24:1841-1848; Chaturvedi et al. (1996) Nucleic Acids Res. 24:2318-2323; and Schultz et al. (1996) Nucleic Acids Res. 24:2966-2973. For example, synthesis of phosphorothioate nucleic acid is similar to that described above for naturally occurring nucleic acids except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190).

Similarly, the synthesis of other phosphate analogs, such as phosphotriester (Miller et al. (1971) JACS 93:6657-6665), non-bridging phosphoramidates (Jager et al. (1988) Biochem. 27:7247-7246), N3' to P5' phosphoramidates (Nelson et al. (1997) JOC 62:7278-7287) and phosphorodithioates (U.S. Pat. No. 5,453,496) has also been described. Other non-phosphorous based modified nucleic acids can also be used (Stirchak et al. (1989) Nucleic Acids Res. 17:6129-6141). Nucleic acids with phosphorothioate backbones can be more resistant, under certain circumstances, to degradation after injection into the host. Braun et al. (1988) J. Immunol. 141:2084-2089; and Latimer et al. (1995) Mol. Immunol. 32:1057-1064.

Nucleic acids useful in the inventions described herein can comprise one or more ribonucleotides (containing ribose as the only or principal sugar component) or, as is known in the art, modified sugars or sugar analogs can be incorporated in the nucleic acids. Thus, in addition to ribose, the sugar moiety can be a one of a class of sugars such as pentose, deoxypentose, hexose, or deoxyhexose; a specific sugar such as glucose, arabinose, xylose, lyxose; or a sugar analog such as a sugar "analog" cyclopentyl group. The sugar can be in pyranosyl or in a furanosyl form. In the recited nucleic acids, the sugar moiety is preferably the furanoside of ribose, arabinose or 2'-O-alkylribose, and the sugar can be attached to the respective heterocyclic bases either in alpha- or beta-anomeric configuration. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications can also be made and combined with any phosphate modification in the preparation of a recited nucleic acid.

The heterocyclic bases, or nucleic acid bases, which are incorporated in the recited nucleic acids can be the naturally-occurring principal purine and pyrimidine bases, (namely uracil, thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the recited nucleic acids can include one or several heterocyclic bases other than the principal five base components of naturally-occurring nucleic acids. In certain implementations, the heterocyclic base in the recited nucleic acids includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

The recited nucleic acids can comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the nucleic acid. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine. Other examples of base modifications include, but are not limited to, addition of an electron-withdrawing moiety to C-5 and/or C-6 of a uracil of the recited nucleic acid. Preferably, the electron-withdrawing moiety is a halogen. Such modified uracils can include, but are not limited to, 5-bromouracil, 5-chlorouracil, 5-fluorouracil, 5-iodouracil.

Other examples of base modifications include the addition of one or more thiol groups to the base including, but not limited to, 6-thio-guanine, 4-thio-thymine and 4-s thio-uracil.

The recited nucleic acids can be synthesized using techniques and nucleic acid synthesis equipment that are well known in the art including, but not limited to, enzymatic methods, chemical methods, and the degradation of larger nucleic acid sequences. See, for example, Ausubel et al. (1987); and Sambrook et al. (1989). When assembled enzymatically, the individual units can be ligated, for example, with a ligase such as T4 DNA or RNA ligase per U.S. Pat. No. 5,124,246. Nucleic acid degradation can be accomplished through the exposure of an nucleic acid to a nuclease, as exemplified in U.S. Pat. No. 4,650,675.

Circular nucleic acids useful in the present invention can be isolated, synthesized through recombinant methods, or chemically synthesized. Where the circular nucleic acid is obtained through isolation or through recombinant methods, the nucleic acid will preferably be a plasmid. The chemical synthesis of smaller circular nucleic acids can be performed using any method described in the literature. See, for instance, Gao et al. (1995) Nucleic Acids Res. 23:2025-2029; and Wang et al. (1994) Nucleic Acids Res. 22:2326-2333.

Techniques for making the recited nucleic acids are known in the art. Naturally occurring DNA containing phosphodiester linkages, is generally synthesized by sequentially coupling the appropriate nucleoside phosphoramidite to the 5'-hydroxy group of the growing nucleic acid attached to a solid support at the 3'-end, followed by oxidation of the intermediate phosphite triester to a phosphate triester. Once the desired nucleic acid sequence has been synthesized, the nucleic acid is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) DNA 3:401 and U.S. Pat. No. 4,458,066.

It is preferred that cytosines of CG motifs present in the recited nucleic acids are not methylated, although other modifications and/or additions are contemplated. However, in certain implementations the recited nucleic acids can contain one or more methylated cytosines that are not part of a CG motif.

The preparation of base-modified nucleosides, and the synthesis of modified nucleic acids using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an nucleic acid. Such base-modified nucleosides, present at either terminal or internal positions of a nucleic acid, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

Nucleic Acid Length Parameters

In some implementations, the recited nucleic acid is less than about any of the following lengths (in bases or base pairs): 10,000; 5,000; 2500; 2000; 1500; 1250; 1000; 750; 500; 300; 250; 200; 175; 150; 125; 100; 75; 50; 25. In some implementations, an immunomodulatory polynucleotide is greater than about any of the following lengths (in bases or base pairs): 24; 30; 40; 50; 60; 75; 100; 125; 150; 175; 200; 250; 300; 350; 400; 500; 750; 1000; 2000; 5000; 7500;

10000; 20000; 50000. Alternately, the immunomodulatory polynucleotide can be any of a range of sizes having an upper limit of 10,000; 5,000; 2500; 2000; 1500; 1250; 1000; 750; 500; 300; 250; 200; 175; 150; 125; 100; 75; 50; or 25; and an independently selected lower limit of 24; 30; 40; 50; 60; 75; 100; 125; 150; 175; 200; 250; 300; 350; 400; 500; 750; 1000; 2000; 5000; 7500, wherein the lower limit is less than the upper limit.

Compositions

The inventive compositions can comprise a variety of materials and substances in addition to the recited nucleic acids. As noted elsewhere herein, such materials and substances can comprise adjuvants, antigens, carriers, pharmaceutically acceptable excipients, and the like.

In certain implementations, carriers useful in the practice of the present inventions comprise protein carriers or synthetic nanocarriers. In implementations, synthetic nanocarriers comprising the inventive composition can be coupled to an antigen. In additional implementations, such synthetic nanocarriers can further comprise an additional synthetic nanocarrier not coupled to the immunostimulatory isolated nucleic acid, and in preferable implementations the additional synthetic nanocarrier is coupled to an antigen.

In certain implementations, the inventive compositions can be administered together with conjugate, or non-conjugate, vaccines. In implementations, the inventive compositions can comprise a carrier peptide or protein, or to another type of carrier. Useful carriers comprise carrier proteins known to be useful in conjugate vaccines, including but not limited to tetanus toxoid (TT), diphtheria toxoid (DT), the nontoxic mutant of diphtheria toxin, CRM197, the outer membrane protein complex from group B *N. meningitidis*, and keyhole limpet hemocyanin (KLH). Other carriers can comprise the synthetic nanocarriers described elsewhere herein, and other carriers that might be known conventionally.

Coupling of antigen or the recited nucleic acids to carriers can be performed using conventional covalent or non-covalent coupling techniques. Useful techniques for developing conjugated vaccines include but are not limited to those generally described in M D Lairmore et al., "Human T-lymphotropic virus type 1 peptides in chimeric and multivalent constructs with promiscuous T-cell epitopes enhance immunogenicity and overcome genetic restriction." J. Virol. October; 69(10):6077-89 (1995); C W Rittershause et al., "Vaccine-induced antibodies inhibit CETP activity in vivo and reduce aortic lesions in a rabbit model of atherosclerosis." Arterioscler Thromb Vasc Biol. September; 20(9):2106-12 (2000); M V Chengalvala et al., "Enhanced immunogenicity of hepatitis B surface antigen by insertion of a helper T cell epitope from tetanus toxoid." Vaccine. March 5; 17(9-10): 1035-41 (1999). N K Dakappagari et al., "A chimeric multi-human epidermal growth factor receptor-2 B cell epitope peptide vaccine mediates superior antitumor responses." J Immunol. April 15; 170(8):4242-53 (2003); J T Garrett et al. "Novel engineered trastuzumab conformational epitopes demonstrate in vitro and in vivo antitumor properties against HER-2/neu." J. Immunol. June 1; 178(11):7120-31 (2007).

In other implementations, the inventive compositions can be combined with antigen, or a conventional vaccine, in a vehicle to form an injectable mixture. The mixtures can be made using conventional pharmaceutical manufacturing and compounding techniques to arrive at useful dosage forms. Techniques suitable for use in practicing the present invention can be found in a variety of sources, including but not limited to M. F. Powell et al., Vaccine Design, 1995 Springer-Verlag publ.; or L. C. Paoletti et al. eds., Vaccines: from Concept to Clinic. A Guide to the Development and Clinical Testing of Vaccines for Human Use 1999 CRC Press publ.

In implementations, synthetic nanocarriers can used as carriers. A wide variety of synthetic nanocarriers can be used according to the invention. In some implementations, synthetic nanocarriers are spheres or spheroids. In some implementations, synthetic nanocarriers are flat or plate-shaped. In some implementations, synthetic nanocarriers are cubes or cubic. In some implementations, synthetic nanocarriers are ovals or ellipses. In some implementations, synthetic nanocarriers are cylinders, cones, or pyramids.

In some implementations, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, can have a minimum dimension or maximum dimension that falls within 5%, 10%, or 20% of the average diameter or average dimension of the synthetic nanocarriers. In some implementations, a population of synthetic nanocarriers can be heterogeneous with respect to size, shape, and/or composition.

Synthetic nanocarriers can be solid or hollow and can comprise one or more layers. In some implementations, each layer has a unique composition and unique properties relative to the other layer(s). To give but one example, synthetic nanocarriers can have a core/shell structure, wherein the core is one layer (e.g., a polymeric core) and the shell is a second layer (e.g., a lipid bilayer or monolayer). Synthetic nanocarriers can comprise a plurality of different layers.

In some implementations, synthetic nanocarriers can optionally comprise one or more lipids. In some implementations, a synthetic nanocarrier can comprise a liposome. In some implementations, a synthetic nanocarrier can comprise a lipid bilayer. In some implementations, a synthetic nanocarrier can comprise a lipid monolayer. In some implementations, a synthetic nanocarrier can comprise a micelle. In some implementations, a synthetic nanocarrier can comprise a core comprising a polymeric matrix surrounded by a lipid layer (e.g., lipid bilayer, lipid monolayer, etc.). In some implementations, a synthetic nanocarrier can comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In some implementations, synthetic nanocarriers can comprise one or more polymers. In some implementations, such a polymer can be surrounded by a coating layer (e.g., liposome, lipid monolayer, micelle, etc.). In some implementations, various elements of the synthetic nanocarriers can be coupled with the polymer.

In some implementations, an immunofeature surface, targeting moiety, and/or nucleic acid can be covalently associated with a polymeric matrix. In some implementations, covalent association is mediated by a linker. In some implementations, an immunofeature surface, targeting moiety, and/or oligonucleotide can be noncovalently associated with a polymeric matrix. For example, in some implementations, an immunofeature surface, targeting moiety, and/or nucleic acid can be encapsulated within, surrounded by, and/or dispersed throughout a polymeric matrix. Alternatively or additionally, an immunofeature surface, targeting moiety, and/or nucleotide can be associated with a polymeric matrix by hydrophobic interactions, charge interactions, van der Waals forces, etc.

A wide variety of polymers and methods for forming polymeric matrices therefrom are known conventionally. In general, a polymeric matrix comprises one or more polymers. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

Examples of polymers suitable for use in the present invention include, but are not limited to polyethylenes, polycarbonates (e.g. poly(1,3-dioxan-2one)), polyanhydrides (e.g. poly(sebacic anhydride)), polypropylfumarates, polyamides (e.g. polycaprolactam), polyacetals, polyethers, polyesters (e.g., polylactide, polyglycolide, polylactide-co-glycolide, polycaprolactone, polyhydroxyacid (e.g. poly($\beta$-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some implementations, polymers in accordance with the present invention include polymers that have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some implementations, polymers can be hydrophilic. For example, polymers can comprise anionic groups (e.g., phosphate group, sulfate group, carboxylate group); cationic groups (e.g., quaternary amine group); or polar groups (e.g., hydroxyl group, thiol group, amine group). In some implementations, a synthetic nanocarrier comprising a hydrophilic polymeric matrix generates a hydrophilic environment within the synthetic nanocarrier. In some implementations, polymers can be hydrophobic. In some implementations, a synthetic nanocarrier comprising a hydrophobic polymeric matrix generates a hydrophobic environment within the synthetic nanocarrier. Selection of the hydrophilicity or hydrophobicity of the polymer can have an impact on the nature of materials that are incorporated (e.g., coupled) within the synthetic nanocarrier.

In some implementations, polymers can be modified with one or more moieties and/or functional groups. A variety of moieties or functional groups can be used in accordance with the present invention. In some implementations, polymers can be modified with polyethylene glycol (PEG), with a carbohydrate, and/or with acyclic polyacetals derived from polysaccharides (Papisov, 2001, ACS Symposium Series, 786:301). Certain implementations can be made using the general teachings of U.S. Pat. No. 5,543,158 to Gref et al., or WO publication WO2009/051837 by Von Andrian et al.

In some implementations, polymers can be modified with a lipid or fatty acid group. In some implementations, a fatty acid group can be one or more of butyric, caproic, caprylic, capric, lauric, myristic, palmitic, stearic, arachidic, behenic, or lignoceric acid. In some implementations, a fatty acid group can be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some implementations, polymers can be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some implementations, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some implementations, polyesters include, for example, poly(caprolactone), poly(caprolactone)-PEG copolymers, poly(L-lactide-co-L-lysine), poly(serine ester), poly(4-hydroxy-L-proline ester), poly[$\alpha$-(4-aminobutyl)-L-glycolic acid], and derivatives thereof.

In some implementations, a polymer can be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some implementations, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some implementations, polymers can be one or more acrylic polymers. In certain implementations, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer can comprise fully-polymerized copolymers of acrylic and methacrylic acid esters with a low content of quaternary ammonium groups.

In some implementations, polymers can be cationic polymers. In general, cationic polymers are able to condense and/or protect negatively charged strands of nucleic acids (e.g., DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In implementations, the inventive synthetic nanocarriers can not comprise (or can exclude) cationic polymers.

In some implementations, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some implementations, polymers can be linear or branched polymers. In some implementations, polymers can be dendrimers. In some implementations, polymers can be substantially cross-linked to one another. In some implementations, polymers can be substantially free of cross-links. In some implementations, polymers can be used in accordance with the present invention without undergoing a cross-linking step. It is further to be understood that inventive synthetic nanocarriers can comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some implementations, synthetic nanocarriers can not comprise a polymeric component. In some implementations, synthetic nanocarriers can comprise metal particles, quantum dots, ceramic particles, etc. In some implementations, a non-polymeric synthetic nanocarrier is an aggregate of non-polymeric components, such as an aggregate of metal atoms (e.g., gold atoms).

In some implementations, synthetic nanocarriers can optionally comprise one or more amphiphilic entities. In some implementations, an amphiphilic entity can promote the production of synthetic nanocarriers with increased stability, improved uniformity, or increased viscosity. In some implementations, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component can be a mixture of different amphiphilic entities. Those skilled in the art will recognize that this is an exemplary, not comprehensive, list of substances with surfactant activity. Any amphiphilic entity can be used in the production of synthetic nanocarriers to be used in accordance with the present invention.

In some implementations, synthetic nanocarriers can optionally comprise one or more carbohydrates. Carbohydrates can be natural or synthetic. A carbohydrate can be a derivatized natural carbohydrate. In certain implementations, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain implementations, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In implementations, the inventive synthetic nanocarriers do not comprise (or specifically exclude) carbohydrates, such as a polysaccharide. In certain implementations, the carbohydrate can comprise a carbohydrate derivative such as a sugar alcohol, including but not limited to mannitol, sorbitol, xylitol, erythritol, maltitol, and lactitol.

In implementations, when preparing carriers for use with the inventive compositions, methods for covalently coupling the recited nucleic acids or other elements of the inventive compositions to the carriers can be useful. In implementations, the recited nucleic acids or other elements of the inventive compositions can be coupled non-covalently to the carriers. If the element to be coupled comprises a small molecule it can be of advantage to attach the element to a polymeric carrier prior to the assembly of synthetic nanocarriers. In implementations, it can be an advantage (for manufacturing or other reasons) to prepare carriers, especially synthetic nanocarriers, with surface groups that are used to couple the adjuvant to the carrier through the use of these surface groups In certain implementations, non-covalent coupling can be accomplished using adsorption. Adsorption of nucleic acids to the surface of a nanoparticle can be accomplished by salt formation. When using this method, the nanoparticle is prepared in such a manner that the nanoparticle comprises a material that introduces a charge to the nanoparticle. Often the use of a charged surfactant, e.g., a cationic surfactant that is used to adsorb the negatively charged nucleic acids during the nanoparticle preparation, is sufficient to provide surface charge to the nanoparticle. Contacting the charged nanoparticles with a solution of nucleic acids causes adsorption of the nucleic acids. This method is described in the patent application in Published International Patent Application WO 00/06123 of O'Hagen et al. Encapsulation of nucleic acids can be accomplished by dissolving the nucleic acids in an aqueous buffer and then using this solution in the single or double emulsion process to form nanoparticles by self assembly. This process is described in Tse, et al *International Journal of Pharmaceutics*, 370 (1-2), 33 (2009). Additional encapsulation methods are described elsewhere herein.

Covalent coupling can be accomplished by a number of methods. These methods are covered in detail in *Bioconjugate Techniques*, 2$^{nd}$ edition, Elsevier (2008) by Hermanson. One method that is particularly suited to coupling nucleic acids to polymers or nanoparticles carrying amine functional groups is to activate the 5' phosphate of the nucleic acid with 1-(3-dimethylamino)propyl-3-ethylcarbodiimide methiodide (EDC) and imidazole and then allowing the activated nucleic acid to react with the amine substituted polymer or nanoparticle [Shabarova et al, *FEBS Letters*, 154 288, (1983)]. This process is shown below for surface amine functionalized nanoparticles.

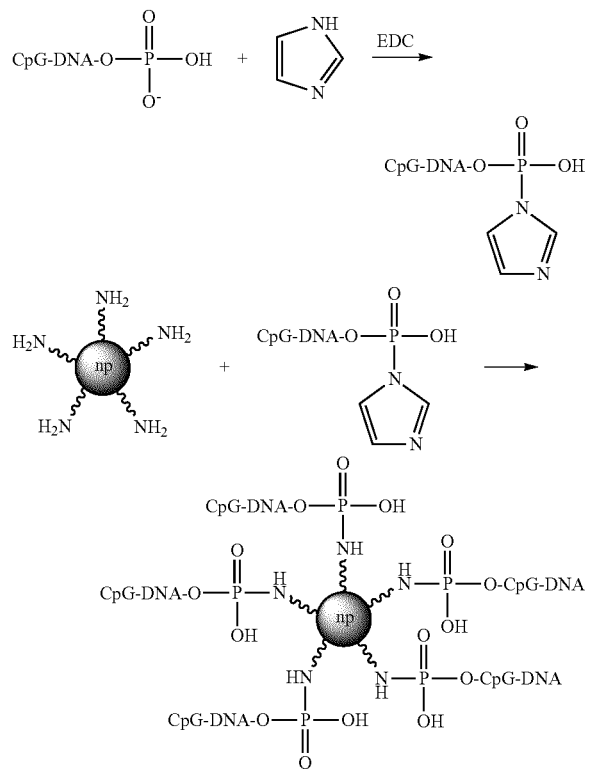

In certain implementations, covalent coupling can be made via a covalent linker. In implementations, the covalent linker can comprise an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one element with the carboxylic acid group of a second element such as the nanocarrier. The amide bond in the linker can be made using any of the conventional amide bond forming reactions with suitably protected amino acids or antigens or adjuvants and activated carboxylic acid such N-hydroxysuccinimide-activated ester.

A disulfide linker is made via the formation of a disulfide (S—S) bond between two sulfur atoms of the form, for instance, of $R_1$—S—S—$R_2$. A disulfide bond can be formed by thiol exchange of an antigen or adjuvant containing thiol/mercaptan group (—SH) with another activated thiol group on an element containing thiol/mercaptan groups with an element containing an activated thiol group.

A triazole linker, specifically a 1,2,3-triazole of the form

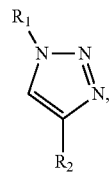

wherein $R_1$ and $R_2$ can be any chemical entities, is made by the 1,3-dipolar cycloaddition reaction of an azide attached to a first element with a terminal alkyne attached to a second element. The 1,3-dipolar cycloaddition reaction is performed with or without a catalyst, preferably with Cu(I)-catalyst, which links the two elements through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click reaction" or CuAAC.

A thioether linker is made by the formation of a sulfur-carbon (thioether) bond in the form, for instance, of $R_1$—S—$R_2$. Thioether can be made by either alkylation of a thiol/mercaptan (—SH) group on one component such as the element with an alkylating group such as halide or epoxide on a second element. Thioether linkers can also be formed by Michael addition of a thiol/mercaptan group on one element to an electron-deficient alkene group on a second element such as a polymer containing a maleimide group as the Michael acceptor. In another way, thioether linkers can be prepared by the radical thiol-ene reaction of a thiol/mercaptan group on one element with an alkene group on a second element such as a polymer or nanocarrier.

A hydrazone linker is made by the reaction of a hydrazide group on one element with an aldehyde/ketone group on the second element.

A hydrazide linker is formed by the reaction of a hydrazine group on one element with a carboxylic acid group on the second element. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one element with an aldehyde or ketone group on a second element.

A urea or thiourea linker is prepared by the reaction of an amine group on one element with an isocyanate or thioisocyanate group on a second element.

An amidine linker is prepared by the reaction of an amine group on one element with an imidoester group on a second element.

An amine linker is made by the alkylation reaction of an amine group on one element with an alkylating group such as halide, epoxide, or sulfonate ester group on the second element. Alternatively, an amine linker can also be made by reductive amination of an amine group on one element with an aldehyde or ketone group on the second element with a suitable reducing reagent such as sodium cyanoborohydride or sodium triacetoxyborohydride.

A sulfonamide linker is made by the reaction of an amine group on one element with a sulfonyl halide (such as sulfonyl chloride) group on a second element.

Elements can also be coupled via non-covalent coupling methods. For examples, a negative charged antigen or adjuvant can be coupled to a positively charged carrier through electrostatic adsorption. An antigen or adjuvant containing a metal ligand can also be coupled to a carrier containing a metal complex via a metal-ligand complex.

In certain implementations, an element such as the recited nucleic acids, an antigen or an adjuvant can be attached to a polymer, for example polylactic acid-block-polyethylene glycol, prior to the assembly of a synthetic nanocarrier or a synthetic nanocarrier can be formed with reactive or activatable groups on its surface. In the latter case, the antigen or adjuvant can be prepared with a group which is compatible with the attachment chemistry that is presented by the synthetic nanocarriers' surface. In other implementations, a peptide antigen can be attached to VLPs or liposomes using a suitable linker.

A linker is a compound or reagent that capable of coupling two molecules together. In an implementation, the linker can be a homobifunctional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide antigen containing an acid group via the other end of the ADH linker on NC to produce the corresponding VLP or liposome peptide conjugate.

Methods of Making and Using the Compositions and Related Methods

Synthetic nanocarriers can be prepared using a wide variety of methods known in the art. For example, synthetic nanocarriers can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755, and also U.S. Pat. Nos. 5,578,325 and 6,007,845).

Various materials can be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006). Other methods suitable for encapsulating materials, such as nucleic acids, into synthetic nanocarriers can be used, including without limitation methods disclosed in U.S. Pat. No. 6,632,671 to Unger issued Oct. 14, 2003; H. Martimprey et al., "Polymer nanocarriers for the delivery of small fragments of nucleic acids: Oligonucleotides and siRNA" European Journal of Pharmaceutics and Biopharmaceutics 71:490-504 (2009); or P. Malyala, et al., "Enhancing the therapeutic efficacy of CpG oligonucleotides using biodegradable microparticles" Advanced Drug Delivery Reviews 61: 218-225 (2009).

In certain implementations, synthetic nanocarriers are prepared by a nanoprecipitation process or spray drying. Conditions used in preparing synthetic nanocarriers can be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used can depend on the materials to be coupled to the synthetic nanocarriers and/or the composition of the polymer matrix.

If particles prepared by any of the above methods have a size range outside of the desired range, particles can be sized, for example, using a sieve.

Elements of the inventive compositions (such as moieties of which an immunofeature surface is comprised, targeting moieties, polymeric matrices, antigens and the like) can be coupled to the overall carrier, e.g., by one or more covalent bonds, or can be coupled by means of one or more linkers. Methods of functionalizing synthetic nanocarriers can be adapted from Published US Patent Application 2006/0002852 to Saltzman et al., Published US Patent Application 2009/0028910 to DeSimone et al., or Published International Patent Application WO 2008/127532 A1 to Murthy et al.

Alternatively or additionally, carriers can be coupled to the recited nucleic acids, immunofeature surfaces, targeting moieties, adjuvants, various antigens, and/or other elements directly or indirectly via non-covalent interactions. In non-covalent implementations, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings can be arranged to be on a portion of a carrier, such as an external surface or an internal surface of an inventive synthetic nanocarrier. In certain implementations, encapsulation and/or absorption is a form of coupling.

In various implementations, the inventive compositions described herein can comprise certain adjuvants, in addition to the inventive immunostimulatory isolated nucleic acids, through admixing in the same vehicle or delivery system. Such adjuvants can include, but are not limited to mineral salts, such as alum, alum combined with monphosphoryl lipid (MPL) A of Enterobacteria, such as *Escherichia coli, Salmonella* minnesota, *Salmonella typhimurium*, or *Shigella flexneri* or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+ squalene+MPL®), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments. The doses of such other adjuvants can be determined using conventional dose ranging studies.

In some implementations, the inventive compositions described herein can be combined with an antigen. Such an antigen can be different from, or similar or identical to those coupled to a nanocarrier (with or without adjuvant, utilizing or not utilizing another delivery vehicle) administered separately at a different time-point and/or at a different body location and/or by a different immunization route or with another antigen and/or adjuvant-carrying composition administered separately at a different time-point and/or at a different body location and/or by a different immunization route.

The inventive compositions can be made using conventional pharmaceutical manufacturing and compounding techniques to arrive at useful dosage forms. Techniques suitable for use in practicing the present invention can be found in *Handbook of Industrial Mixing Science and Practice*, Edited by Edward L. Paul, Victor A. Atiemo-Obeng, and Suzanne M. Kresta, 2004 John Wiley & Sons, Inc.; and *Pharmaceutics: The Science of Dosage Form Design,* 2nd Ed. Edited by M. E. Auten, 2001, Churchill Livingstone. In some implementations, inventive compositions are formulated in sterile saline solution for injection together with a preservative.

It is to be understood that the compositions of the invention can be made in any suitable manner, and the invention is in no way limited to compositions that can be produced using the methods described herein. Selection of an appropriate method can require attention to the properties of the particular materials and substances being utilized.

In some implementations, inventive compositions are manufactured under sterile conditions or are terminally sterilized. This can ensure that resulting compositions are sterile and non-infectious, thus improving safety when compared to non-sterile compositions. This provides a valuable safety measure, especially when subjects receiving inventive compositions have immune defects, are suffering from infection, and/or are susceptible to infection. In some implementations, inventive compositions can be lyophilized and stored in suspension or as lyophilized powder depending on the formulation strategy for extended periods without losing activity.

The inventive compositions described herein can be administered by a variety of routes of administration, including but not limited to subcutaneous, intramuscular, intradermal, oral, intranasal, transmucosal, sublingual, rectal, ophthalmic, transdermal, transcutaneous or by a combination of these routes.

The amount of recited nucleic acids present in the inventive dosage forms can be varied according to the nature of the recited nucleic acids, the therapeutic benefit to be accomplished, and other such parameters. In some implementations, dose ranging studies can be conducted to establish optimal therapeutic amount of the recited nucleic acids, and the amount of various antigens that can be present in the inventive compositions. In various implementations, the recited nucleic acids are present in the composition in an amount effective to generate an immune response to the recited nucleic acids upon administration to a subject. It can be possible to determine amounts of the recited nucleic acids effective to generate an immune response using conventional dose ranging studies and techniques in subjects. Inventive compositions can be administered at a variety of frequencies. In a preferred implementation, at least one administration of the inventive composition is sufficient to generate a pharmacologically relevant response. In more preferred implementation, at least two administrations, at least three administrations, or at least four administrations, of the inventive composition are utilized to ensure a pharmacologically relevant response.

The compositions and methods described herein can be used to induce, enhance, modulate, direct, or redirect an immune response. The compositions and methods described herein can be used in the diagnosis, prophylaxis and/or treatment of conditions such as cancers, infectious diseases, metabolic diseases, degenerative diseases, autoimmune diseases, inflammatory diseases, immunological diseases, or other disorders and/or conditions. The compositions and methods described herein can also be used for the prophylaxis or treatment of an addiction, such as an addiction to nicotine or a narcotic. The compositions and methods described herein can also be used for the prophylaxis and/or treatment of a condition resulting from the exposure to a toxin, hazardous substance, environmental toxin, or other harmful agent.

EXAMPLES

Example 1

Nucleic Acids

There are three types of CpG nucleic acid molecules (types A, B and C). Type A CpG nucleic acids are strong inducers of IFN-α. Type B CpG nucleic acids are strong activators of B-cells, and induce expression of IL-6, but are poor inducers of IFN-α. Type C CpG nucleic acid molecules have characteristics of both Type A and B CpG nucleic acids. Type C CpG nucleic acids induce expression of IL-6, and induce expression of IFN-α. IFN-α activates APC and drives B-cell activation and differentiation. Type C CpG nucleic acids also stimulate plasmacytoid dendritic cells which enhance B-cell and plasma cell development. The characteristics of type C CpG nucleic acid molecules therefore potentially make them a superior adjuvant over types A and B.

Selecta-7, an immunostimulatory nucleic acid having nucleotide sequence

[SEQ ID NO: 1]
5'-TCGTCGAACGTTCGCGAACGTTCG-3' and having a phosphorothioated backbone was designed to have characteristics of type C CpG nucleic acid molecules and was synthesized using standard oligo-synthesis techniques (Beaucage, S.; Iyer, R. (1992). Tetrahedron 48: 2223. doi:10.1016/S0040-4020(01)88752-4; Brown, D. M. A brief history of oligonucleotide synthesis. Methods in Molecular Biology (Totowa, N.J., United States) (1993), 20 (Protocols for Oligonucleotides and Analogs), 1-17; Reese, Colin B. (2005). "Oligo- and poly-nucleotides: 50 years of chemical synthesis". Organic & Biomolecular Chemistry 3: 3851. doi: 10.1039/b510458k; Iyer, R. P.; Beaucage, S. L. 7.05. Oligonucleotide synthesis. In: Comprehensive Natural Products Chemistry, Vol. 7: DNA and Aspects of Molecular Biology. Kool, Eric T.; Editor. Neth. (1999), 733 pp. Publisher: (Elsevier, Amsterdam, Neth.), 105-152).

Figure 1B:
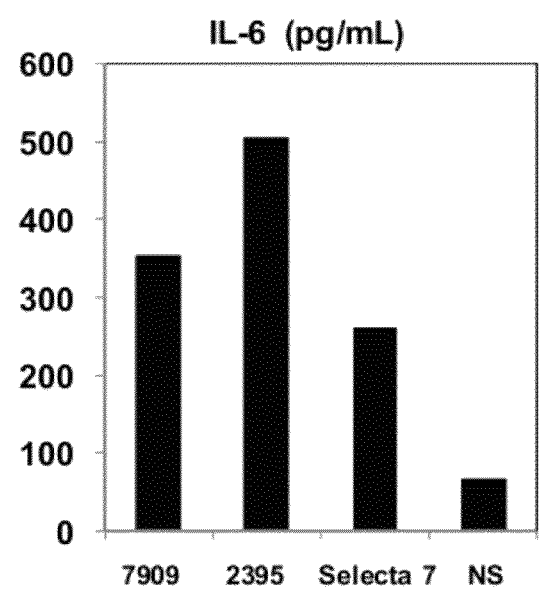
Figure 1C:
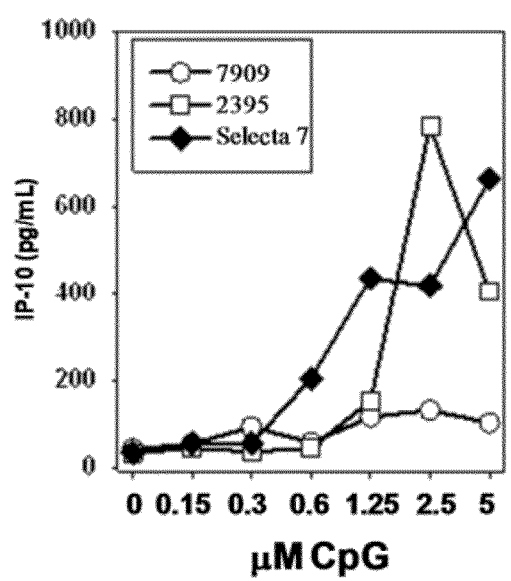
FIGS. 1C-1D are line graphs depicting dose response of cytokine levels (1C, IP-10; 1D, IL-6) as measured by ELISA of peripheral blood mononuclear cells stimulated in the presence of the indicated concentrations of CpG oligonucleotides.
Figure 1D:
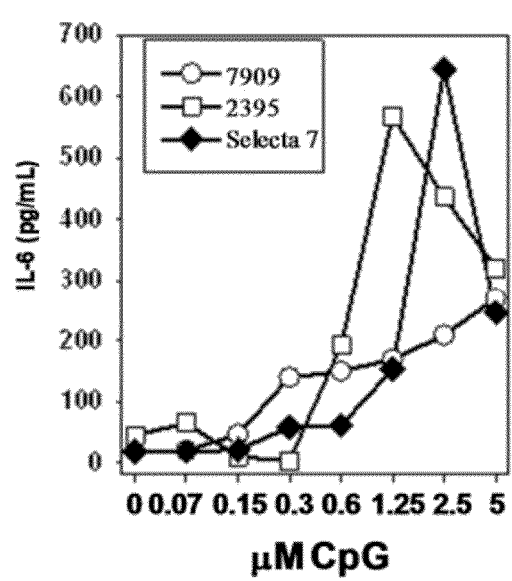

Selecta-7 was compared to previously known phosphorothioated 7909 (type B—see, e.g., Cooper et al. (2004) J Clinical Immunology 24(6): 693-701) and 2395 (Type C—see description above) for the ability to induce expression of IFN-α, IP-10 and IL-6 by ELISA (FIGS. 1A-1D). Human peripheral blood mononuclear cells were isolated and cultured in the presence or absence of CpG. 24 hours later supernatants were collected and evaluated by ELISA. All CpGs tested were able to up-regulate expression of IL-6 (FIGS. 1B, 1D). However the B-type CpG 7909 did not increase expression of IFN-α (FIG. 1A), or IP-10 (FIG. 1C), whereas both Selecta-7 and 2395 did (FIGS. 1A, 1C). Overall the data suggests that Selecta-7 is a novel C-type CpG.

Figure 2:
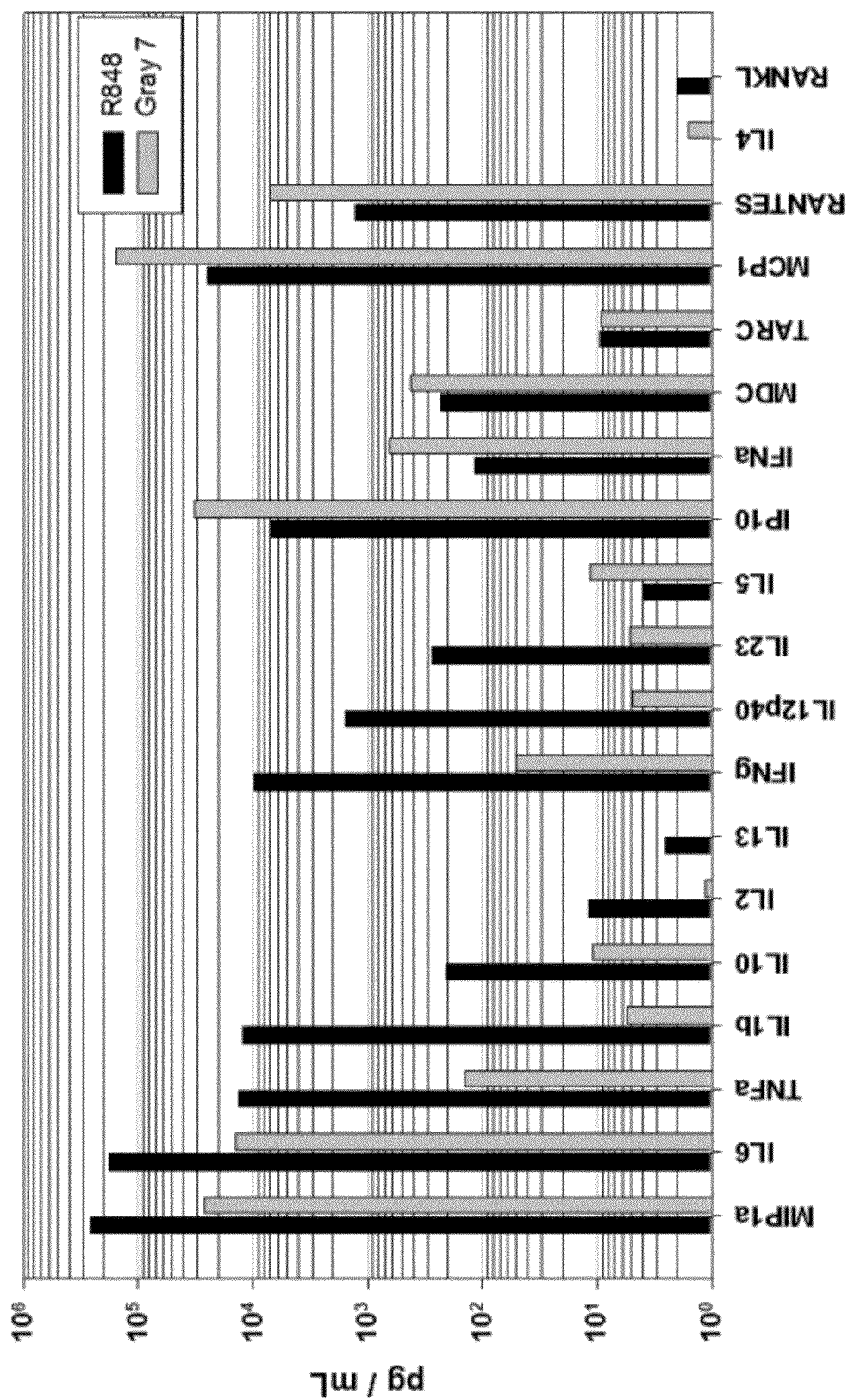
FIG. 2 is a bar graph showing cytokine profiles of peripheral blood mononuclear cells in the presence of Selecta-7 or R848.

CpG nucleic acid molecules stimulate cells through TLR9, while the small molecule agonist R848 signals through TLRs 7 and 8. Because TLRs 7 and 9 are expressed on plasmacytoid dendritic cells, while TLR8 is expressed on myeloid dendritic cells the response between R848 (Resiquimod) and Selecta-7 should be different. To test this, human peripheral blood mononuclear cells were isolated and cultured in the presence or absence of R848 or Selecta-7. 24 hours later supernatants were collected and evaluated by cytokine and chemokine multiplex analysis. The analytes were the cytokines: IL-6, TNF-α, IL-1β, IL-10, IL-2, IL-13, IFN-γ, IL-12p40, IL23, IL-5, IP-10, RANKL, IL-4; and chemokines: MDC, RANTES, IP-10, and Mip-1α. The data show a differential response between R848 and Selecta-7. R848 is a potent inducer of pro-inflammatory cytokines such as IL-6, MIP-1α, RANTES, IFN-γ, IL-10, IL-12p40, TNF-α, and IL-23, whereas Selecta-7 was a potent inducer of IFN-α, IP-10 and IL-5 (FIG. 2). The data show that R848 and Selecta-7 have a substantially different cellular response with different cytokine profiles from stimulated PBMCs.

Example 2

Synthetic Nanocarriers with Coupled Nucleic Acids

An inventive composition comprising synthetic nanocarriers that comprise the recited Selecta-7 immunostimulatory isolated nucleic acid is prepared as follows:

Selecta-7, a novel immunostimulatory isolated single-stranded nucleic acid having the deoxyribonucleotide sequence:

[SEQ ID NO: 1]
5'-TCGTCGAACGTTCGCGAACGTTCG-3' with a sodium counter-ion is purchased from Oligo Factory (Holliston, Mass.).

PLGA with 76% lactide and 24% glycolide content and an inherent viscosity of 0.49 dL/g is purchased from SurModics Pharmaceuticals (Birmingham, Ala.; Product Code 7525 DLG 5A.) PLA-PEG block co-polymer with a PEG block of approximately 5,000 Da and PLA block of approximately 20,000 Da is obtained from Selecta Biosciences (Watertown Mass.). Polyvinyl alcohol (Mw=11,000-31,000, 87-89% hydrolyzed) is purchased from J. T. Baker (Part Number U232-08).

Solutions are prepared as follows:

Solution 1: immunostimulatory isolated nucleic acid of [SEQ ID NO:1] at 100 mg/mL is prepared in purified water.

Solution 2: 0.49-IV 7525 PLGA @ 75 mg/mL and PLA-PEG @ 25 mg/ml in dichloromethane. The solution is made by first preparing two separate solutions at room temperature: 0.49-IV 7525 PLGA @ 100 mg/mL in pure dichloromethane and PLA-PEG @ 100 mg/mL in pure dichloromethane. The final solution is prepared by adding 3 parts PLGA solution for each part of PLA-PEG solution.

Solution 3: Polyvinyl alcohol @ 50 mg/mL in 100 mM pH 8 phosphate buffer.

Solution 4: 70 mM phosphate buffer, pH 8

A primary (W1/O) emulsion is first created using Solution 1 & Solution 2. Solution 1 (0.1 mL) and Solution 2 (1.0 mL) are combined in a small glass pressure tube and sonicated at 50% amplitude for 40 seconds using a Branson Digital Sonifier 250.

A secondary (W1/O/W2) emulsion is then formed by adding Solution 3 (3.0 mL) to the primary emulsion and sonicating at 30% amplitude for 60 seconds using the Branson Digital Sonifier 250.

The second emulsion is added to a beaker containing 70 mM phosphate buffer solution (30 mL) and stirred at room temperature for 2 hours to allow for the dichloromethane to evaporate and for the nanocarriers to form in suspension. A portion of the suspended nanocarriers is washed by transferring the nanocarrier suspension to a centrifuge tube, spinning at 21,000 rcf for 45 minutes, removing the supernatant, and re-suspending the pellet in phosphate buffered saline. This washing procedure is repeated and then the pellet is re-suspended in phosphate buffered saline to achieve final nanocarrier suspension having a nominal concentration of 10 mg/mL on a polymer basis.

The amount of oligonucleotide in the nanocarrier is determined by RP-HPLC analysis. The total dry-nanocarrier mass per mL of suspension is determined by a gravimetric method. The final nanocarrier concentration is achieved by dilution to 5 mg/mL with additional phosphate buffered saline.

Example 3

Protein Carriers with Covalently Coupled Nucleic Acids

Phosphorothioated sulfhydryl-modified nucleic acid of SEQ ID NO:1 is prepared by solid-phase synthesis. Ovalbumin (OVA, chicken egg albumin, grade VI from Sigma (St. Louis, Mo.)) is activated with a 20-fold molar excess of m-maleimidobenzoyl-N-hydroxy-sulfo-succinimide ester (sulfo-MBS, Pierce) in a 5-mM EDTA-PBS buffer pH 7.0 for 2.5 h at room temperature. The amino groups of L-lysine residues on the OVA are modified with maleimide groups. Unbound sulfo-MBS is removed chromatographically on a Bio-Econo P6 gel column (Bio-Rad, Munich, Germany). The sulfhydryl-modified nucleic acid of SEQ ID NO:1 is then reduced in a 50 mM 1,4-dithiothreitol-PBS solution at room temperature for 2 h and residual reagents removed by chromatography on a Bio-Econo P6 gel column.

The resulting nucleic acid is then incubated with modified OVA at a molar ratio of 5:1 for 3 hours at room temperature and L-cysteine is then added to quench reactive maleimide groups. Free nucleic acid is removed by dialysis against PBS (MWCO10000, Pierce). The dialyzed product is desalted by chromatography on a PD-10 desalting column, followed by lyophilization. The resulting nucleic acid-Ova Conjugates are analyzed on a 6-20% gradient SDS-PAGE (silver stain) and a 4-15% gradient non-denaturing, non-reducing PAGE (ethidium bromide). Protein concentration is determined using the Lowry method (Pierce).

Example 4

Nucleic Acids

Additional immunostimulatory isolated nucleic acids that include the following sequences are synthesized using conventional solid state synthetic techniques. The backbones of the sequences are phosphodiester backbones.

```
5'-TCGTCGAACGTTCGCGAACGTTCGAACGTT-3'                          [SEQ ID NO: 2]

5'-TCGTCGAACGTTCGCGAACGTTCGAACGTTAACGTT-3'                    [SEQ ID NO: 3]

5'-TCGTCGAACGTTCGCGAACGTTCGTCGTCGAACGTTCGCGAACGTTCG-3'        [SEQ ID NO: 4]

5'-TCGTCGAACGTTCGCGAACGTTCGTTCGAA-3'                          [SEQ ID NO: 5]

5'-TCGTCGAACGTTCGCGAACGTTCGGACGTC-3'                          [SEQ ID NO: 6]

5'-TCGTCGAACGTTCGCGAACGTTCGATCGAT-3'                          [SEQ ID NO: 7]
```

The above sequences are also synthesized with phosphorothioated backbones to stabilize the DNA. Any of the above sequences are combined with suitable excipient(s) to form inventive compositions.

Example 5

Preparation of Nanocarriers with Nucleic Acids

A composition comprising synthetic nanocarriers that comprise the disclosed immunostimulatory isolated nucleic acid was prepared as follows:

Selecta-7, a novel immunostimulatory isolated single-stranded nucleic acid having the deoxyribonucleotide sequence:

```
                                                              [SEQ ID NO: 1]
            5'-TCGTCGAACGTTCGCGAACGTTCG-3'
``` was purchased from Oligo Factory (Holliston, Mass.)

Solutions were prepared as follows:

Solution 1: immunostimulatory isolated nucleic acid of SEQ ID NO:1 at 40 mg/mL in 150 mM KCl.

Solution 2: 0.50 mL 7525 PLGA (Lakeshore Biomaterials) @ 100 mg/mL, 0.25 mL 5050 PLGA (Lakeshore Biomaterials) @ 100 mg/mL, and 0.25 mL PLA-PEG-Nicotine (Selecta Biosciences) @ 100 mg/ml in dichloromethane.

Solution 3: Polyvinyl alcohol (Lakeshore Biomaterials) @ 5% in 100 mM pH 8 phosphate buffer.

Solution 4: 70 mM phosphate buffer, pH 8

A primary (W1/O) emulsion was first created using Solution 1 & Solution 2. Solution 1 (0.25 mL) and Solution 2 (1.0 mL) were combined in a small glass pressure tube and sonicated at 50% amplitude for 40 seconds using a Branson Digital Sonifier 250.

A secondary (W1/O/W2) emulsion was then formed by adding Solution 3 (3.0 mL) to the primary emulsion and sonicating at 30% amplitude for 60 seconds using the Branson Digital Sonifier 250.

The second emulsion was added to a beaker containing 70 mM phosphate buffer solution (30 mL) and stirred at room temperature for 2 hours to allow for the dichloromethane to evaporate and for the nanocarriers to form in suspension. A portion of the suspended nanocarriers was washed by transferring the nanocarrier suspension to a centrifuge tube, spinning at 21,000 rcf for 45 minutes, removing the supernatant, and re-suspending the pellet in phosphate buffered saline. This washing procedure was repeated and then the pellet was re-suspended in phosphate buffered saline to achieve final nanocarrier suspension having a nominal concentration of 8.1 mg/mL on a polymer basis.

The nucleic acid-containing nanoparticles were blended with nanoparticles containing T-cell helper peptide (TCHP; SEQ ID NO:13 of US 2011/0110965) prepared as follows:

Solutions were prepared as follows:

Solution 1: TCHP (Bachem) at 30 mg/mL was prepared in 60% v/v lactic acid.

Solution 2: 0.75 mL PLA (Lakeshore Biomaterials) @ 100 mg/mL and 0.25 mL PLA-PEG-Nicotine (Selecta Biosciences) @ 100 mg/ml in dichloromethane.

Solution 3: Polyvinyl alcohol (JT Baker) @ 5% in 100 mM pH 8 phosphate buffer.

Solution 4: 70 mM phosphate buffer, pH 8

A primary (W1/O) emulsion was first created using Solution 1 & Solution 2. Solution 1 (0.25 mL) and Solution 2 (1.0 mL) were combined in a small glass pressure tube and sonicated at 50% amplitude for 40 seconds using a Branson Digital Sonifier 250.

The secondary (W1/O/W2) emulsion was then formed by adding Solution 3 (3.0 mL) to the primary emulsion and sonicating at 30% amplitude for 60 seconds using the Branson Digital Sonifier 250.

The second emulsion was added to a beaker containing 70 mM phosphate buffer solution (30 mL) and stirred at room temperature for 2 hours to allow for the dichloromethane to evaporate and for the nanocarriers to form in suspension. A portion of the suspended nanocarriers was washed by transferring the nanocarrier suspension to a centrifuge tube, spinning at 21,000 rcf for 45 minutes, removing the supernatant, and re-suspending the pellet in phosphate buffered saline. This washing procedure was repeated and then the pellet was re-suspended in phosphate buffered saline to achieve final nanocarrier suspension having a nominal concentration of 8.1 mg/mL on a polymer basis.

The two nanoparticle suspensions at 8.1 mg/mL each were blended 1:1 to form a synthetic nanocarrier mixture (NP-7) for further studies.

Example 6

Nucleic Acids Augment Antibody Response In Vivo

Figure 3:
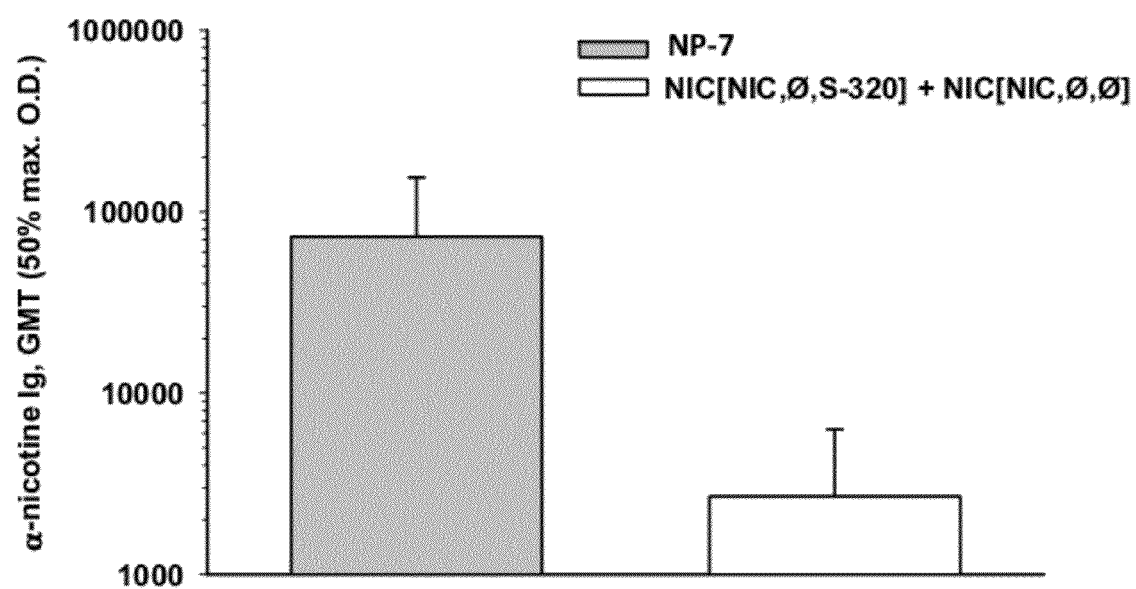
FIG. 3 is a bar graph depicting antibody titers of mice administered nanoparticles containing nicotine and Selecta-7 (NP-7) or a similar nicotine nanoparticle mixture that did not contain an adjuvant (NP[NIC,Ø,S-320]+NP[NIC,Ø,Ø]).

Immunization with a mixture of nicotine NP with entrapped Selecta-7 (SEQ ID NO:1), the synthetic nanocarrier mixture NP-7 as prepared in Example 5 was compared to immunization with a similar nicotine NP mixture that did not contain an adjuvant (NP[NIC,Ø,Ø]+NP[NIC,Ø,S-320]). Mice were immunized subcutaneously on days 0, 14, and 28 with 100 µg of NP-7 or with control NP NP[NIC,Ø,Ø]+NP[NIC,Ø,S-320]. For each immunization dose, NP-7 contained 7.4 µg of Selecta-7. Serum anti-nicotine antibody titers were measured by ELISA at day 26 (FIG. 3). Addition of nicotine NP with entrapped Selecta-7 augmented the antibody response to nicotine by a factor of 25. Thus, the disclosed nucleic acids are active in vivo and NP-7 including Selecta-7 induced a strong antibody response to nicotine in mice.

Example 7

Nanoparticles Containing Nucleic Acids Induce Antibody Responses in Non-Human Primates A mixture of nicotine NP with entrapped Selecta-7 (SEQ ID NO:1, NP-7) as prepared in Example 5 was administered to non-human primates to study induction of antibody responses. Animals received a total of three vaccinations with a 4-week interval in between NP-7 injections (see detailed schedule below). At each procedure time point, the animals were sedated with 10 mg/kg ketamine-HCl administered intramuscularly. 1 ml of the test substance was administered via the subcutaneous route. Briefly, the skin on the quadriceps was shaved, wiped with alcohol and allowed to dry. The immunizing material was then administered via a 23 gauge, 1-inch needle. The animals were monitored and returned to their home cage when awake. The animals were weighed when sedated for each procedure. Blood samples and 5 ml of serum (used for antibody analysis) were collected at approximately bi-weekly intervals according to the following schedule:

Pre bleed: day—14
First vaccination: day 0
Phlebotomy: day 14
Second vaccination: day 28
Phlebotomy: day 42
Third vaccination: day 56
Phlebotomy: day 70
Phlebotomy day 84

Serum samples were aliquoted, stored at $-20°$ C., and assayed for anti-nicotine and anti-carrier antibodies by ELISA. For measurement of anti-nicotine antibodies, 96-well ELISA plates were coated with polylysine-nicotine and incubated overnight at $4°$ C. For measurement of anti-carrier antibodies, 96-well ELISA plates were coated with either polylysine-PEG diluted 1:100 or base nanoparticles diluted 1:1000 (same formulation as used for injections except base nanoparticles do not contain nicotine) and incubated overnight at $4°$ C. Plates were washed and blocked for 2 hours at room temperature with 10% FBS in PBS. Plates were washed and serum samples were added to top row of ELISA plates and diluted in 10% FBS in PBS 3-fold down the plate. A monoclonal mouse anti-nicotine antibody was used as a standard positive control in two columns on each plate for polylysine-nicotine coated plates. For polylysine-PEG and base nanoparticle coated plates, a monoclonal rabbit anti-PEG antibody was used as a positive control. For negative controls, isotype control antibodies or serum from unimmunized animals were used. After serum sample addition, plates were incubated for 2 hours at room temperature. Plates were washed and biotinylated anti-monkey IgG was added to the plates. For mouse antibody standards, biotinylated goat anti-mouse Ig (total) was added to the plates. Plates were incubated for 1 hour at room temperature, washed, and streptavidin-horseradish peroxidase (SA-HRP) was added to the plates. After 30 minutes incubation at room temperature, plates were washed and TMB substrate was added. Plates were incubated in the dark for 15 minutes at room temperature, stop solution (2N $H_2SO_4$) was added to the plates, and OD readings at 450 and 570 nm were taken using a plate reader. The half maximal effective concentration ($EC_{50}$) of anti-nicotine antibody based on the generated four-parameter logistic curve-fit graph was calculated for each sample.

Affinities of serum antibodies to nicotine were measured by equilibrium dialysis assays using 3H-labeled nicotine. $K_d$ (antibody affinity) and $B_{max}$ (antibody concentration) were determined based on a free vs. bound ligand saturation curve. Affinity measurements in monkeys were done on day 70, 14-days after the second boost.

Figure 4:
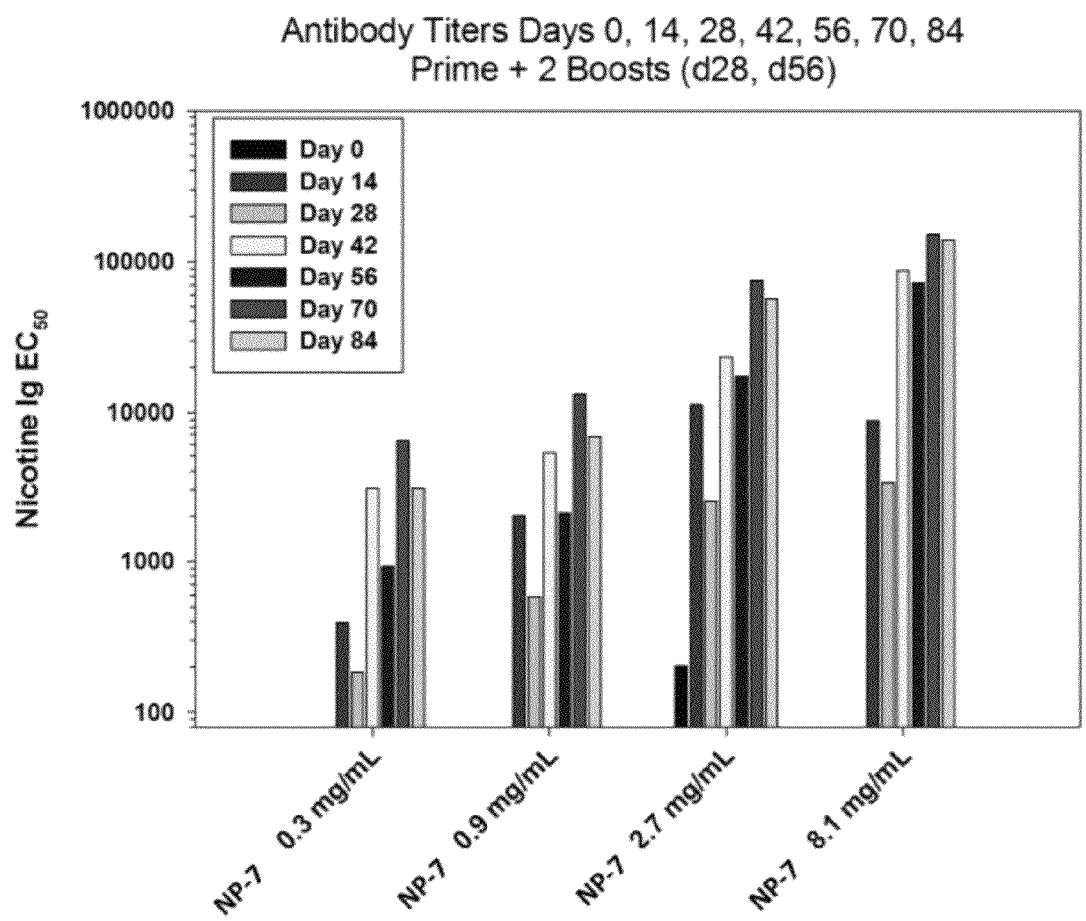
FIG. 4 is a bar graph depicting antibody titers of non-human primates at the indicated dates administered the indicated doses of nanoparticles containing nicotine and Selecta-7 (NP-7).

NP-7 (0.9-8.1 mg) induced antibodies against nicotine in a dose-dependent manner. Considerable titers (50,000-150,000) persisted in the animals immunized with the three highest doses of NP-7 at least for 2 months after the last boost. NP-7 antibody response was dose-dependent throughout the duration of experiment (FIG. 4). The data show that NP-7, containing Selecta-7 as the adjuvant was able to induce a robust dose dependent antibody response in non-human primates.

OTHER IMPLEMENTATIONS

A number of implementations of the invention have been described. Nevertheless, it will be understood that various modifications can be made without departing from the spirit and scope of the invention. Accordingly, other implementations are within the scope of the following claims.

What is claimed is:

1. A composition comprising:
   an immunostimulatory isolated nucleic acid comprising a sequence:

5'-TCGTCGAACGTTCGCGAACGTTCG-3'; [SEQ ID NO. 1]

and
   a pharmaceutically acceptable excipient;
   wherein C is unmethylated.

2. The composition of claim 1, wherein the immunostimulatory isolated nucleic acid further comprises a stabilizing modification.

3. The composition of claim 2, wherein the stabilizing modification comprises modifications of 3' OH or 5' OH groups, modifications of nucleotide bases, modifications of sugar components, or modifications of phosphate groups.

4. The composition of claim 2, wherein the stabilizing modification comprises a phosphorothioate backbone.

5. The composition of claim 1, further comprising an antigen.

6. The composition of claim 5, wherein the antigen comprises a B cell antigen.

7. The composition of claim 5, wherein the antigen comprises a T cell antigen.

8. The composition of claim 7, wherein the T cell antigen comprises a T helper cell antigen.

9. The composition of claim 6, wherein the B cell antigen comprises one or more of a protein, peptide, small molecule, and a carbohydrate.

10. The composition of claim 1, further comprising a carrier coupled to the immunostimulatory isolated nucleic acid.

11. The composition of claim 10, wherein the carrier comprises a protein carrier.

12. The composition of claim 10, wherein the carrier comprises a synthetic nanocarrier.

13. The composition of claim 12, wherein the synthetic nanocarrier is additionally coupled to an antigen.

14. The composition of claim 12, further comprising an additional synthetic nanocarrier not coupled to the immunostimulatory isolated nucleic acid.

15. The composition of claim 14, wherein the additional synthetic nanocarrier is coupled to an antigen.

16. The composition of claim 15, wherein the antigen comprises a T helper cell antigen.

17. The composition of claim 1, wherein the immunostimulatory isolated nucleic acid consists essentially of:

5'-TCGTCGAACGTTCGCGAACGTTCG-3'. [SEQ ID NO. 1]

18. The composition of claim 1, wherein the immunostimulatory isolated nucleic acid does not comprise a stabilizing modification.

19. The composition of claim 1, wherein the immunostimulatory nucleic acid consists of SEQ ID NO:1.

20. A method of inducing IL-6 production in a subject, the method comprising administering to the subject the composition of claim 1 in an amount effective amount to induce IL-6 in the subject.

21. A method for inducing interferon-alpha in a subject, the method comprising administering to the subject the composition of claim 1 in an amount effective to induce interferon-alpha production in the subject.

22. A method for inducing IP-10 in a subject, the method comprising administering to the subject the composition of claim 1 in an amount effective to induce IP-10 production in the subject.

23. A method comprising:
    administering the composition of claim 1 to a subject.

24. A composition comprising
    a vaccine that comprises the composition of claim 1.

25. An isolated nucleic acid comprising SEQ ID NO:1.

26. An isolated nucleic acid consisting of SEQ ID NO:1.

27. A method comprising:
    administering to a subject an amount of the composition of claim 6 effective to induce an antibody response against the antigen.

* * * * *